United States Patent [19]
Baltz et al.

[11] 4,304,856
[45] Dec. 8, 1981

[54] PROCESS FOR PRODUCING 20-DIHYDRO-20-DEOXY-23-DEMYCINOSYLTYLOSIN

[75] Inventors: Richard H. Baltz; Herbert A. Kirst; Gene M. Wild, all of Indianapolis, Ind.; Eugene T. Seno, Norwich, England

[73] Assignee: Eli Lilly and Company, Indianapolis, Ind.

[21] Appl. No.: 205,539

[22] Filed: Nov. 10, 1980

[51] Int. Cl.³ .................... C12P 19/62; C12N 1/20; C12R 1/54
[52] U.S. Cl. .................... 435/76; 435/253; 435/896
[58] Field of Search .................... 435/76, 253, 896

[56] References Cited

U.S. PATENT DOCUMENTS

| | | | |
|---|---|---|---|
| 3,178,341 | 4/1965 | Hamill et al. | 424/120 |
| 3,326,759 | 6/1967 | Hamill et al. | 424/120 |
| 3,344,024 | 9/1967 | Whaley et al. | 424/120 |
| 3,459,853 | 8/1969 | Gorman et al. | 424/121 |
| 4,056,616 | 11/1977 | Reimann et al. | 424/180 |
| 4,161,523 | 7/1979 | Weinstein et al. | 424/181 |
| 4,196,280 | 4/1980 | Umezawa et al. | 536/17 R |
| 4,252,898 | 2/1981 | Nash et al. | 435/76 |

OTHER PUBLICATIONS

Kinumaki et al., Journal of Antibiotics 30 (6) 450–454 (1977).
Derwent Abstract 86252x/46 of Japanese Examined Patent 6037-351.
Yamaguchi et al., Journal of Antibiotics 31(5) 433–440 (1978).
Derwent Abstract 86253x/46 of Japanese Examined Patent 6037-352.
Tsukiura et al., Journal of Antibiotics 22 (3) 89–99 (1969).
Suzuki et al., Chemistry Letters 1973, 793–798.
Nash et al., Current Chemotherapy and Infectious Disease Proceedings of 11th ICC and the 19th ICAAC Amer. Soc. Microbiology pp. 462–463 (1980).
Nagel et al., Journal of Organic Chemistry 44 (12) 2050–2052 (1979).
Masamune et al., Journal Amer. Chem. Soc. 98 (24), 7874–7875 (1976).
Chemical Abstract 93: 68663u (1980) Abstr. of Japan Kokai 80 43,0183.

*Primary Examiner*—Lionel M. Shapiro
*Attorney, Agent, or Firm*—Nancy J. Harrison; Arthur R. Whale

[57] ABSTRACT

20-Dihydro-20-deoxy-23-demycinosyltylosin (DH-DO-DMT), 20-dihydro-20-deoxy-5-O-mycaminosyltylonolide (DH-DO-OMT), specified acyl ester derivatives, and their acid addition salts are useful intermediates and antibacterial agents. Methods of preparing DH-DO-DMT and DH-DO-OMT by fermentation of *Streptomyces fradiae* and the microorganism *S. fradiae* ATCC 31733 are included.

6 Claims, 2 Drawing Figures

PROCESS FOR PRODUCING 20-DIHYDRO-20-DEOXY-23-DEMYCINOSYL-TYLOSIN

SUMMARY OF THE INVENTION

This invention relates to 20-dihydro-20-deoxy-23-demycinosyltylosin, and to 20-dihydro-20-deoxy-5-O-mycaminosyltylonolide, two new macrolide antibiotics. 20-Dihydro-20-deoxy-23-demycinosyltylosin, which will be called DH-DO-DMT for convenience herein, has structure 1:

[Chemical structure 1]

Although no stereochemical assignments are indicated in the structures given herein, the stereochemistry of the compounds is identical to that of tylosin. The neutral sugar in structure 1 is mycarose, and the amino-sugar in 1 is mycaminose.

20-Dihydro-20-deoxy-5-O-mycaminosyltylonolide, which will be called DH-DO-OMT for convenience herein, has structure 2:

[Chemical structure 2]

DH-DO-DMT and DH-DO-OMT inhibit the growth of organisms which are pathogenic to animals. More specifically, DH-DO-DMT and DH-DO-OMT are antibacterial agents which are active against gram-positive microorganisms and Mycoplasma species.

DH-DO-DMT can be esterified on the 2', 4'', 3'', 23 and 3-hydroxyl groups and DH-DO-OMT can be esterified on the 2', 4', 23 and 3-hydroxyl groups to form useful acyl ester derivatives. Esterification of the 2'- and 4'-hydroxyl groups is most facile. Typical esters are those of a monocarboxylic acid or hemi-esters of a dicarboxylic acid having from 2 to 18 carbon atoms.

DH-DO-DMT, DH-DO-OMT and their acyl ester derivatives are basic compounds which, when treated with acids, are converted to acid addition salts. These acid addition salts are also part of this invention.

This invention further relates to a new microorganism which has been classified as a strain of *Streptomyces fradiae* and to the method of producing DH-DO-DMT or DH-DO-OMT by culturing this strain under submerged aerobic fermentation conditions until a substantial level of antibiotic activity is produced. DH-DO-DMT and DH-DO-OMT can be extracted from basified broth filtrate with polar organic solvents, and can be further purified by extraction, chromatographic and/or crystallization techniques.

This invention also relates to a method of preparing DH-DO-OMT by mild acid hydrolysis of DH-DO-DMT.

DESCRIPTION OF THE DRAWINGS

The infrared absorption spectra of DH-DO-DMT (free base) and DH-DO-OMT (free base) in chloroform are presented in the accompanying drawings as follows.

DETAILED DESCRIPTION

The following paragraphs describe the properties of DH-DO-DMT and DH-DO-OMT.

DH-DO-DMT

The structure of DH-DO-DMT is shown in formula 1.

DH-DO-DMT is a white crystalline solid with a melting point of about 198°–200° C. DH-DO-DMT has the following approximate percentage elemental composition: carbon, 63%; hydrogen, 9%; nitrogen, 2%;

oxygen, 26%. DH-DO-DMT has an empirical formula of $C_{38}H_{65}NO_{12}$ and a molecular weight of about 728 (727 as determined by field-desorption mass spectrometry).

Figure 1:
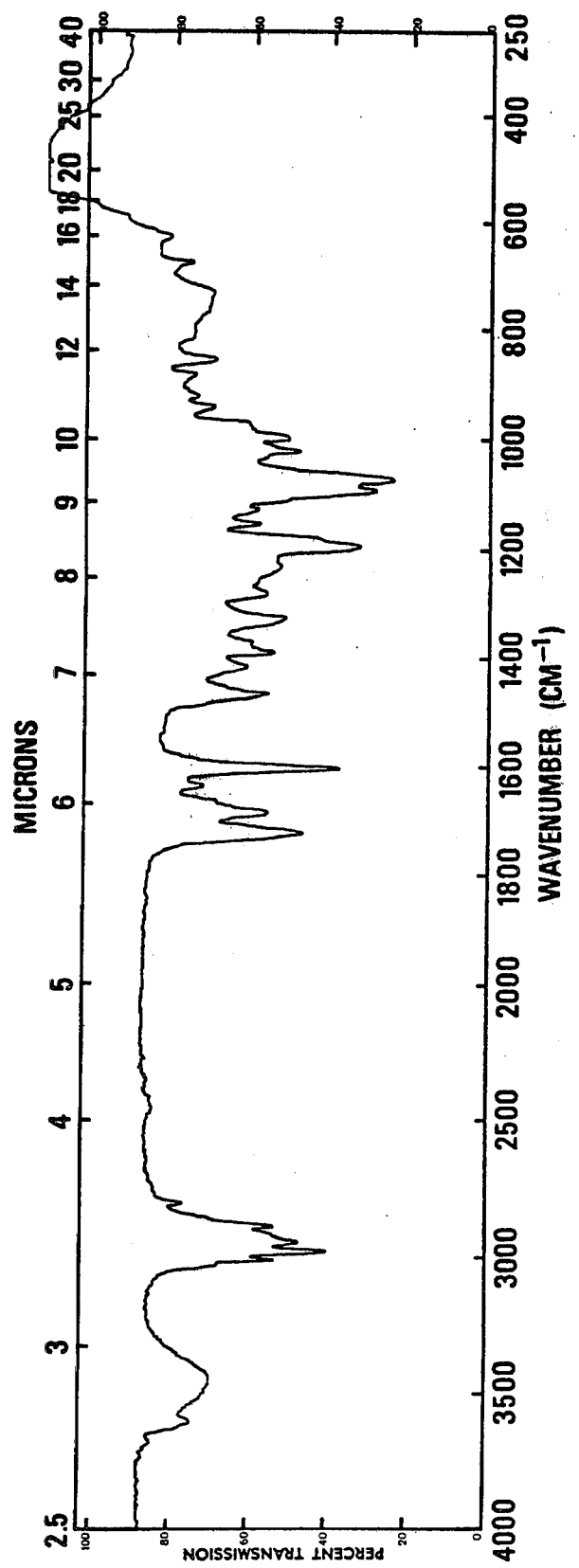
FIG. 1—DH-DO-DMT
FIG. 2—DH-DO-OMT

The infrared absorption spectrum of DH-DO-DMT free base in chloroform is shown in FIG. 1 of the accompanying drawings. Observable absorption maxima occur at the following frequencies (cm$^{-1}$): 3676 (small), 3598 (small), 3470 (large broad), 3010 (intense), 2974 (intense), 2938 (intense), 2925 (shoulder), 2880 (intense), 2799 (small), 2457 (small broad), 1715 (intense), 1676 (medium), 1629 (small), 1595 (very intense), 1456 (intense), 1411 (intense), 1380 (intense), 1363 (shoulder), 1315 (intense), 1273 (small), 1263 (shoulder), 1220 (small broad), 1184 (intense), 1162 (intense), 1144 (small), 1117 (medium), 1096 (shoulder), 1076 (intense/shoulder), 1050 (very intense), 1015 (intense), 997 (medium), 986 (medium), 958 (medium), 923 (medium) 905 (medium), 867 (small), 842 (medium), 720 (broad) and 660 (small).

The ultraviolet absorption spectrum of DH-DO-DMT in 95% neutral ethanol exhibits an absorption maximum at 283 nm ($\epsilon$21,800).

DH-DO-DMT (free base) has the following specific rotation: $[\alpha]_D^{25} = 46.3°$ (c 3.3, $CH_3OH$).

DH-DO-OMT

DH-DO-OMT is a white crystalline solid with a melting point of about 214°–217° C. DH-DO-OMT has the following approximate percentage elemental composition: carbon, 64%; hydrogen, 9%; nitrogen, 2.5%; oxygen, 24.5%. DH-DO-OMT has an empirical formula of $C_{31}H_{53}NO_9$ and a molecular weight of about 584 (583 by field-desorption mass spectrometry).

Figure 2:
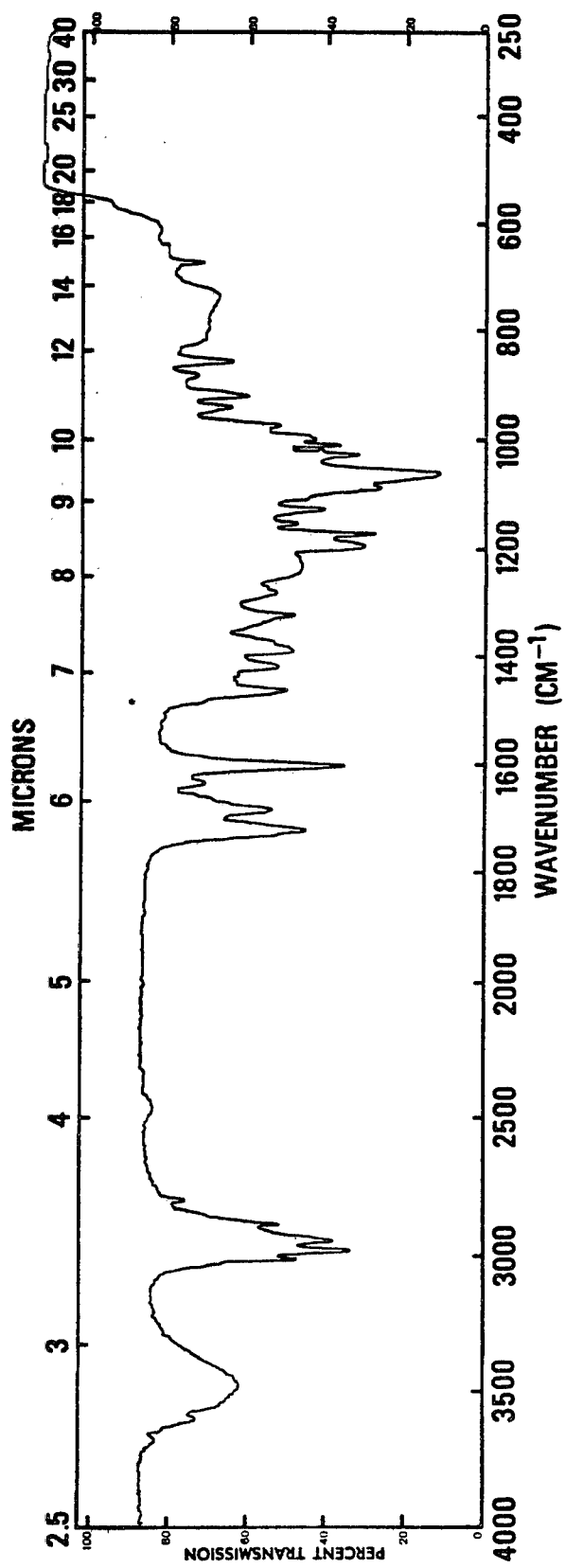

The infrared absorption spectrum of DH-DO-OMT free base in chloroform is shown in FIG. 2 of the accompanying drawings. Observable absorption maxima occur at the following frequencies (cm$^{-1}$): 3677 (very small), 3601 (small), 3422 (broad), 3006 (intense), 2971 (intense), 2937 (intense), 2879 (intense), 2798 (small), 1714 (intense), 1677 (intense), 1627 (small), 1593 (very intense), 1457 (intense), 1407 (small), 1382 (medium), 1362 (shoulder), 1315 (medium), 1269 (small), 1181 (very intense), 1141 (small), 1115 (small), 1181 (very intense), 1141 (small), 1115 (small), 1079 and 1058 (intense, doublet), 1008 (medium), 983 (medium), 923 (small), 903 (small), 865 (small), 835 (small), 712 (broad), 658 (small) and 629 (small).

The ultraviolet absorption spectrum of DH-DO-OMT in 95% neutral ethanol exhibits an absorption maximum at 282 nm ($\epsilon$22,400).

DH-DO-OMT (free base) has the following specific rotation: $[\alpha]_D^{25} = -7.35$ (c 6, $CH_3OH$).

The $^1H$ nuclear magnetic resonance (NMR) data at 360 MHz for DH-DO-OMT (free base) in $CDCl_3$ are summarized in Table 1.

TABLE 1

| 360 MHz NMR Data for DH—DO—OMT | |
|---|---|
| Position | δ* |
| 2 | 2.02/2.5 |
| 3 | ~3.7–3.85 |
| 4 | 1.64 |
| 5 | ~3.7–3.85 |
| 6 | NA** |
| 7 | NA |
| 8 | 2.8 |
| 10 | 6.27 |
| 11 | 7.27 |
| 13 | 5.78 |
| 14 | 2.91 |

TABLE 1-continued

| 360 MHz NMR Data for DH—DO—OMT | |
|---|---|
| Position | δ* |
| 15 | 4.96 |
| 16 | NA/1.64 |
| 17 | 0.96 |
| 18 | 1.05 |
| 19 | 1.49 |
| 20 | 0.89 |
| 21 | 1.18 |
| 22 | 1.82 |
| 23 | ~3.7–3.85 |
| 1' | 4.31 |
| 2' | 3.55 |
| 3' | 2.40 |
| 4' | 3.08 |
| 5' | 3.22 |
| 6' | 1.31 |
| NMe$_2$ | 2.51 |

*ppm downfield from internal tetramethylsilane
**NA means not assigned

DH-DO-DMT and DH-DO-OMT as free bases are soluble in water and in most polar organic solvents such as acetone, methanol, ethanol, chloroform, dimethylformamide and dimethyl sulfoxide. Acid addition salts of DH-DO-DMT and DH-DO-OMT are more soluble in water than are the free bases.

DH-DO-DMT and DH-DO-OMT can be distinguished by thin-layer chromatography (TLC). The approximate Rf values of DH-DO-DMT and DH-DO-OMT in one TLC system are summarized in Table 2. Ultraviolet absorption was used for detection.

TABLE 2

| Thin-Layer Chromatography Data[a,b] | |
|---|---|
| Compound | Rf Value |
| DH—DO—OMT | 0.53 |
| DH—DO—DMT | 0.64 |

[a]Medium: E. Merck, Darmstadt - Silica Gel 60
[b]Solvent: ethyl acetate:diethylamine (95:5)

Preparation of DH-DO-OMT

This invention also relates to a method of preparing DH-DO-OMT by mild acid hydrolysis of DH-DO-DMT. Mild acid hydrolysis conditions are known in the art. Appropriate solutions having a pH of about four or below can be used to accomplish the hydrolysis. Temperatures of about 20° to about 100° C. can be used in this method. The reaction time needed to carry out the hydrolysis varies, depending upon the pH of the reaction mixture and the temperature used. At higher pH levels the reaction rate is slower, and at higher temperatures the reaction rate is faster. The reaction is carried out by treating DH-DO-DMT with a mild acid solution for a time sufficient to effect removal of the mycarosyl group to give DH-DO-OMT.

Alternatively, and sometimes preferably, DH-DO-OMT can be prepared by treating DH-DO-DMT in the fermentation broth in which it is produced, using mild acidic conditions as described above for a time sufficient to convert the DH-DO-DMT to DH-DO-OMT. DH-DO-OMT thus prepared can be isolated from the fermentation broth using techniques herein described.

Ester Derivatives

DH-DO-DMT can be esterified on the 2', 4'', 3'', 23 and 3-hydroxyl groups to give acyl ester derivatives by treatment with acylating agents using methods known in the art. DH-DO-OMT can be esterified on the 2', 4', 23 and 3-hydroxyl groups. Typical acylating agents include anhydrides, halides (usually in combination with a base or other acid scavenger) and active esters of organic acids. Acylation can also be achieved by using a mixture of an organic acid and a dehydrating agent such as N,N'-dicyclohexylcarbodiimide. Acylations can also be carried out enzymatically as described by Okamoto et al. in U.S. Pat. No. 4,092,473. Once formed, the acyl derivatives can be separated and purified by known techniques.

Esterification of the 2'- and 4'-hydroxyl groups is most facile. Thus, esterification of DH-DO-DMT gives 2'-monoester derivatives by selective esterification techniques generally known in the art, such as, for example, treatment of the antibiotic with a stoichiometric quantity (or a slight excess) of an acylating agent, such as an acyl anhydride, at about room temperature for from about 1 to about 24 hours until esterification is substantially complete. These derivatives can be isolated from the reaction mixture by standard procedures such as extraction, chromatography and crystallization. Esterification of DH-DO-OMT under similar conditions gives 2',4'-diester derivatives. 2'-Monoesters of DH-DO-OMT are prepared by hydrolyzing the corresponding 2'-monoesters of DH-DO-DMT, using mildly acidic conditions as described above. Mixed 2',4'-diesters of DH-DO-OMT are then prepared by esterification of the 2'-monoesters of DH-DO-OMT as described above.

Useful esters are those of organic acids including aliphatic, cycloaliphatic, aryl, aralkyl, heterocyclic carboxylic, sulfonic and alkoxycarbonic acids of from 2 to 18 carbon atoms, and of inorganic acids, such as sulfuric and phosphoric acids.

Representative suitable esters include those derived from acids such as acetic, chloroacetic, propionic, butyric, isovaleric, alkoxycarbonic, stearic, cyclopropanecarboxylic, cyclohexanecarboxylic, $\beta$-cyclohexylpropionic, 1-adamantanecarboxylic, benzoic phenylacetic, phenoxyacetic, mandelic and 2-thienylacetic acids, and alkyl-, aryl-, and aralkyl-sulfonic acids. The aryl- and aralkyl-acids optionally possess substituents such as halogen, nitro, lower alkoxy and the like on the aromatic moiety. Suitable esters also include hemiesters derived from dicarboxylic acids such as succinic, maleic, fumaric, malonic and phthalic acids.

Pharmaceutically acceptable ester derivatives are a preferred group. Other ester derivatives are useful, however, as intermediates.

Salts

DH-DO-DMT, DH-DO-OMT and their specified derivatives form acid addition salts. The acid addition salts of DH-DO-DMT and DH-DO-OMT and of their acyl derivatives are also part of this invention. Such salts are useful, for example, for separating, purifying and crystallizing DH-DO-DMT, DH-DO-OMT and their acyl derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic and the like acids.

Pharmaceutically acceptable acid addition salts are an especially preferred group of salts of this invention. "Pharmaceutically acceptable" salts are those which may be administered safely and effectively to warm-blooded animals.

Preparation of DH-DO-DMT and DH-DO-OMT by *S. fradiae*

DH-DO-DMT and DH-DO-OMT are prepared by culturing a strain of *Streptomyces fradiae*, such as *S. fradiae* ATCC 31733, which produces these compounds under submerged aerobic conditions in a suitable culture medium until substantial antibiotic activity is produced. The culture medium used to grow *Streptomyces fradiae* ATCC 31733 can be any one of a number of media. For economy in production, optimal yield, and ease of product isolation, however, certain culture media are preferred. Thus, for example, preferred carbon sources in large-scale fermentation include carbohydrates such as dextrin, glucose, starch, and corn meal, and oils such as soybean oil. Preferred nitrogen sources include corn meal, soybean meal, fish meal, amino acids and the like. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M.W. about 2000) to large-scale fermentation media if foaming becomes a problem.

For production of substantial quantities of DH-DO-DMT or DH-DO-OMT, submerged aerobic fermentation in tanks is preferred. Small quantities of DH-DO-DMT or DH-DO-OMT may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the vegetative inoculum can be the same as that used for larger fermentations, but other media can also be used.

*S. fradiae* ATCC 31733 can be grown at temperatures between about 10° and about 40° C. Optimum antibiotic production appears to occur at temperatures of about 28° C.

As is customary in aerobic submerged culture processes, sterile air is bubbled through the culture medium. For efficient antibiotic production the percent of air saturation for tank production should be about 30% or above (at 28° C. and one atmosphere of pressure).

Antibiotic production can be followed during the fermentation by testing samples of the broth against organisms known to be sensitive to these antibiotics. One useful assay organism is *Staphylococcus aureus* ATCC 9144. The bioassay is conveniently performed by an automated turbidometric method. In addition, antibiotic production can be readily monitored by highperformance liquid chromatography with UV detection.

Following its production under submerged aerobic fermentation conditions, DH-DO-DMT or DH-DO-OMT can be recovered from the fermentation medium by methods used in the art. Recovery of DH-DO-DMT or DH-DO-OMT is accomplished by an initial filtration of the fermentation broth. The filtered broth can then be further purified to give the desired antibiotic. A variety of techniques may be used in this purification. A preferred technique for purification of the filtered broth involves adjusting the broth to about pH 9; extracting the broth with a suitable solvent such as ethyl acetate, amyl acetate, or methyl isobutyl ketone; extracting the organic phase with an aqueous acidic solution; and precipitating the antibiotic by making the aqueous extract basic. Further purification involves the use of extraction, chromatographic and/or precipitation techniques.

The new microorganism which produces DH-DO-DMT and DH-DO-OMT was obtained by chemical mutagenesis of a *Streptomyces fradiae* strain which produced tylosin. The new microorganism produces only minimal amounts of tylosin, but produces DH-DO-DMT and DH-DO-OMT in approximately equal amounts as major components.

The new DH-DO-DMT- and DH-DO-OMT-producing microorganism is also classified as *Streptomyces fradiae*. A culture of the new microorganism has been deposited and made part of the stock culture collection of The American Type Culture Collection, 12301 Parklawn Drive, Rockville, Md., 20852, from which it is available to the public under the accession number ATCC 31733.

As is the case with other organisms, the characteristics of *Streptomyces fradiae* ATCC 31733 are subject to variation. For example, artificial variants and mutants of the ATCC 31733 strain may be obtained by treatment with various known physical and chemical mutagens, such as ultraviolet rays, X-rays, gamma rays, and N-methyl-N'-nitro-N-nitrosoguanidine. All natural and artificial variants, mutants and recombinants of *Streptomyces fradiae* ATCC 31733 which retain the characteristic of production of DH-DO-DMT and/or DH-DO-OMT may be used in this invention.

DH-DO-DMT and DH-DO-OMT inhibit the growth of pathogenic bacteria, especially gram-positive bacteria and Mycoplasma species. Table 3 summarizes the minimal inhibitory concentrations (MIC), as measured by standard agar-dilution assays, at which DH-DO-DMT and DH-DO-OMT (as free bases) inhibit certain bacteria.

TABLE 3

| In Vitro Activity of DH—DO—DMT and DH—DO—OMT | | |
|---|---|---|
| | MIC (µg/ml) | |
| Organism | DH—DO—DMT | DH—DO—OMT |
| Staphylococcus aureus NRRL B313 | 128 | 4 |
| Staphylocoocccus aureus V41 | 128 | 4 |
| Staphylococcus aureus X400 | >128 | 8 |
| Staphylococcus aureus S13E | 64 | 4 |
| Staphylococcus epidermidis EPI1 | 128 | 8 |
| Staphylococcus epidermidis EPI2 | 64 | 8 |
| Streptococcus pyogenes C203 | >128 | 8 |
| Streptococcus pneumoniae Park 1 | >128 | 8 |
| Streptococcus faecium ATCC 9790 | >128 | 16 |
| Streptococcus sp. group D 9960 | >128 | 16 |
| Haemophilus influenzae C.L. | >128 | 16 |
| Haemophilus influenzae 76 | >128 | 16 |
| Shigella sonnei N9 | >128 | >128 |
| Escherichia coli N10 | >128 | >128 |
| Escherichia coli EC14 | >128 | >128 |
| Escherichia coli TEM | >128 | 64 |
| Klebsiella pneumoniae X26 | >128 | 4 |
| Klebsiella pneumoniae KAE | >128 | >128 |

DH-DO-OMT also inhibits certain anaerobic bacteria. Table 4 summarizes the MIC's at which DH-DO-OMT inhibits these bacteria. The MIC's were determined using a standard agar-dilution assay and reading the end point after 24 hours.

TABLE 4

| In Vitro Activity of DH—DO—OMT Against Anaerobic Bacteria | |
|---|---|
| Organism | MIC (µg/ml) |
| Clostridium difficile 2294 | 2 |
| Clostridium perfringens 81 | 2 |
| Clostridium septicum 1128 | 2 |
| Eubacterium aerofaciens 1235 | 2 |
| Peptococcus asaccharolyticus 1302 | >8 |
| Peptococcus prevoti 1281 | >8 |
| Peptostreptococcus anaerobius 1428 | >8 |
| Peptostreptococcus intermedius 1264 | >8 |
| Propionibacterium acnes 79 | 2 |
| Bacteroides fragilis 111 | >8 |
| Bacteroides fragilis 1877 | >8 |
| Bacteroides fragilis 1936B | >8 |
| Bacteroides thetaiotaomicron 1438 | >8 |
| Bacteroides melaninogenicus 1856/28 | >8 |
| Bacteroides melaninogenicus 2736 | >8 |
| Bacteroides vulgatis 1211 | >8 |
| Bacteroides corrodens 1874 | >8 |
| Fusobacterium symbiosum 1470 | >8 |
| Fusobacterium necrophorum 6054A | 8 |

DH-DO-OMT also inhibits *Chlamydia trachomatis* grown in cell culture with an MIC of 0.5 µg/ml. In addition, DH-DO-OMT inhibits Mycoplasma species. For example, DH-DO-OMT had an MIC value of 12.5 µg/ml against both *M. gallisepticum* and *M. synoviae*.

DH-DO-OMT has shown in vivo antimicrobial activity against experimental bacterial infections. When two doses of test compound were administered to mice in experimental infections, the activity observed was measured as an $ED_{50}$ value [effective dose in mg/kg to protect 50% of the test animals: see Warren Wick, et al., *J. Bacteriol.* 81, 233-235 (1961)]. The $ED_{50}$ values observed for DH-DO-OMT (free base) are given in Table 5.

TABLE 5
In Vivo Activity of DH—DO—OMT against Experimental Infections in Mice

| Organism | Route of Administration | Bacterial Challenge ($LD_{50}$) | $ED_{50}$ (mg/kg × 2) |
|---|---|---|---|
| *Staphylococcus aureus* 3055 | oral | 100 | 44 |
| *Staphylococcus aureus* 3055 | subcutaneous | 221 | 37.3 |
| *Streptococcus pyogenes* C203 | oral | 64 | 75.3 |
| *Streptococcus pneumoniae* Park I | oral | 20.4 | 223.6 |

Although DH-DO-DMT and its derivatives have some antibacterial activity, these compounds are best used as intermediates to the corresponding DH-DO-OMT compounds.

DH-DO-OMT, the acyl ester derivatives of DH-DO-OMT and their acid addition salts can also be used as surface disinfectants. Solutions containing as little as 0.01% by weight are useful for disinfecting purposes. Such solutions, preferably also containing a detergent or other cleansing agent, are useful for disinfecting objects and surfaces where maintenance of sterile conditions is important.

In order to illustrate more fully the operation of this invention, the following examples are provided:

EXAMPLE 1

A. Shake-flask Fermentation of DH-DO-DMT and DH-DO-OMT

A lyophilized pellet of *Streptomyces fradiae* ATCC 31733 is dispersed in 1-2 ml of sterilized water. A portion of this solution (0.5 ml) is used to inoculate a vegetative medium (150 ml) having the following composition:

| Ingredient | Amount (%) |
|---|---|
| Corn steep liquor | 1.0 |
| Yeast extract | 0.5 |
| Soybean grits | 0.5 |
| $CaCO_3$ | 0.3 |
| Soybean oil (crude) | 0.45 |
| Deionized water | 97.25 |

Alternatively, a vegetative culture of *S. fradiae* ATCC 31733 preserved, in 1-ml volumes, in liquid nitrogen is rapidly thawed and used to inoculate the vegetative medium. The inoculated vegetative medium is incubated in a 500-ml Erlenmeyer flask at 29° C. for about 48 hours on a closed-box shaker at 300 rpm.

This incubated vegetative medium (0.5 ml) is used to inoculate 7 ml of a production medium having the following composition:

| Ingredient | Amount (%) |
|---|---|
| Beet molasses | 2.0 |
| Corn meal | 1.5 |
| Fish meal | 0.9 |
| Corn gluten | 0.9 |
| NaCl | 0.1 |
| $(NH_4)_2HPO_4$ | 0.04 |
| $CaCO_3$ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of DH-DO-DMT and DH-DO-OMT

In order to provide a larger volume of inoculum, 1200 ml of incubated vegetative medium, prepared in a manner similar to that described in section A, is used to inoculate 250 gallons of a second-stage vegetative growth medium having the following composition:

| Ingredient | Amount (%) |
|---|---|
| Corn steep liquor | 1.0 |
| Soybean oil meal | 0.5 |
| Yeast extract | 0.5 |
| $CaCO_3$ | 0.3 |
| Soybean oil (crude) | 0.5 |
| Lecithin (crude) | 0.015 |
| Water | 97.185 |

Adjust pH to 8.5 with 50% NaOH solution.

This second-stage vegetative medium is incubated in a 350-gallon tank for about 48 hours at 28° C., with adequate aeration and agitation.

Incubated second-stage medium (144 gallons) thus prepared is used to inoculate 1000 gallons of sterile production medium having the following composition:

| Ingredient | Amount (%) |
|---|---|
| Fish meal | 0.875 |
| Corn meal | 1.5 |
| Corn gluten | 0.875 |
| $CaCO_3$ | 0.2 |
| NaCl | 0.1 |
| $(NH_4)_2HPO_4$ | 0.04 |
| Beet molasses | 2.0 |
| Soybean oil (crude) | 3.0 |
| Lecithin | 0.09 |
| Water | 91.32 |

Adjust pH to 7.2 with 50% NaOH solution.

The inoculated production medium is allowed to ferment in a 1600-gallon tank for 8 to 9 days at a temperature of 28° C. The fermentation medium is aerated with sterile air to keep the dissolved oxygen level between about 30% and 50% and is stirred with conventional agitators at about 250 rpm.

EXAMPLE 2

Isolation of DH-DO-DMT and DH-DO-OMT

Whole broth (38 L), prepared as described in Example 1, section B, is filtered using a filtration aid. The mycelial cake is washed with water; and the filtrate and wash solution (30 L) is adjusted to pH 9.1 with 10% sodium hydroxide. The resulting solution is extracted twice with ethyl acetate (15 L and 5.5 L). The ethyl acetate extracts are combined and extracted with 9 L and then 3 L of a dilute phosphoric acid solution (water phase adjusted to pH 4.1 by the addition of 28% $H_3PO_4$). The combined aqueous extracts (8.8 L), adjusted to pH 9.2 with sodium hydroxide, are extracted twice with chloroform (2 L each). The chloroform extracts are dried to give 32 g of solid material.

A portion of this material (5 g) is dissolved in ethyl acetate and treated, using a six-stage countercurrent distribution procedure, with ethyl acetate and 0.5 M phosphate buffer at pH 6.1 to give 2.5 g of DH-DO- OMT. A second six-stage procedure at pH 5.5 gives an additional 0.1 g of DH-DO-OMT. DH-DO-OMT is crystallized from dry acetone.

These procedures also give 1.42 g of impure DH-DO-DMT. In order to purify DH-DO-DMT a countercurrent system consisting of an organic phase of ethyl acetate:heptane (1:2) and an aqueous phase of 0.5 M phosphate buffer at pH 6.2 is used. Six stages give partial separation of DH-DO-DMT. DH-DO-DMT is crystallized from aqueous methanol. From 1 g of crude material, 400 mg of purified DH-DO-DMT is obtained.

EXAMPLE 3

Preparation of DH-DO-OMT from DH-DO-DMT

DH-DO-DMT, prepared as described in Example 2, is dissolved in a dilute hydrochloric acid solution (HCl added to the water solution until the pH of the solution is 1.8). The resulting solution is allowed to stand for 24 hours at room temperature and then is adjusted to pH 9.0 by the addition of sodium hydroxide. This basic solution is extracted with ethyl acetate, dichloromethane or chloroform. The extract is dried and evaporated under vacuum to give DH-DO-OMT.

EXAMPLE 4

Alternative Preparation of DH-DO-OMT

DH-DO-OMT is prepared from DH-DO-DMT by treating the DH-DO-DMT in the fermentation broth in which it is produced with mild acid as described in Example 3. Isolation of the DH-DO-OMT is accomplished by a procedure similar to that described in Example 2.

EXAMPLE 5

2'-O-Propionyl-DH-DO-DMT

DH-DO-DMT is dissolved in acetone and treated with 1.2 equivalents of propionic anhydride at room temperature for about six hours to give 2'-O-propionyl-DH-DO-DMT.

EXAMPLES 6-9

2'-O-Isovaleryl-DH-DO-DMT, prepared according to the procedure of Example 5, but using isovaleric anhydride.

2'-O-Benzoyl-DH-DO-DMT, prepared according to the procedure of Example 5 but using benzoic anhydride.

2'-O-(n-Butyryl)DH-DO-DMT, prepared according to the procedure of Example 5, but using n-butyric anhydride.

2'-O-Acetyl-DH-DO-DMT, prepared according to the procedure of Example 5 but using acetic anhydride.

EXAMPLE 10

2'-O-Propionyl-DH-DO-OMT, prepared by hydrolyzing 2'-O-propionyl-DH-DO-DMT of Example 5 using the procedure of Example 3.

EXAMPLES 11-14

2'-O-Isovaleryl-DH-DO-OMT, prepared according to the procedure of Example 10, but using 2'-O-isovaleryl-DH-DO-DMT.

2'-O-Benzoyl-DH-DO-OMT, prepared according to the procedure of Example 10, but using 2'-O-benzoyl-DH-DO-DMT.

2'-O-(n-Butyryl)-DH-DO-OMT, prepared according to the procedure of Example 10, but using 2'-O-(n-butyryl)DH-DO-DMT.

2'-O-Acetyl-DH-DO-OMT, prepared according to the procedure of Example 10, but using 2'-O-acetyl-DH-DO-DMT.

EXAMPLE 15

2',4'-Di-O-acetyl-DH-DO-OMT, prepared by the procedure described in Example 5, but using about 2 to 2.5 equivalents of acetic anhydride and DH-DO-OMT as the starting material.

EXAMPLES 16-19

2',4'-Di-O-propionyl-DH-DO-OMT, prepared according to the procedure of Example 15, but using propionic anhydride.

2',4'-Di-O-isovaleryl-DH-DO-OMT, prepared according to the procedure of Example 15, but using isovaleric anhydride.

2',4'-Di-O-benzoyl-DH-DO-OMT, prepared according to the procedure of Example 15, but using benzoic anhydride.

2',4'-Di-O-(n-butyryl)-DH-DO-OMT, prepared according to the procedure of Example 15, but using n-butyric anhydride.

EXAMPLE 20

2'-O-Acetyl-4'-O-isovaleryl-DH-DO-OMT, prepared by treating 2'-O-acetyl-DH-DO-OMT of Example 14 with isovaleric anhydride, using the procedure of Example 5.

EXAMPLES 21-24

2'-O-Acetyl-4'-O-propionyl-DH-DO-OMT, prepared by treating the 2'-O-acetyl-DH-DO-OMT of Example 14 with propionic anhydride, using the procedure of Example 5.

2'-O-Propionyl-4'-O-isovaleryl-DH-DO-OMT, prepared by treating the 2'-O-propionyl-DH-DO-OMT of Example 10 with isovaleric anhydride, using the procedure of Example 5.

2'-O-Isovaleryl-4'-O-acetyl-DH-DO-OMT, prepared by treating 2'-O-isovaleryl-DH-DO-OMT of Example 11 with acetic anhydride, using the procedure of Example 5.

2'-O-Benzoyl-4'-O-acetyl-DH-DO-OMT, prepared by treating 2'-O-benzoyl-DH-DO-OMT of Example 12 with acetic anhydride using the procedure of Example 5.

We claim:

1. The method of producing the antibiotics 20-dihydro-20-deoxy-23-demycinosyltylosin and 20-dihydro-20-deoxy-5-O-mycaminosyltylonolide which comprises cultivating *Streptomyces fradiae* ATCC 31733 or a mutant or recombinant thereof which produces said antibiotics in a culture medium containing assimilable sources of carbon, nitrogen, and inorganic salts under submerged aerobic fermentation conditions until a substantial amount of antibiotic activity is produced.

2. The method of claim 1 which comprises cultivating *Streptomyces fradiae* ATCC 31733.

3. The method of claim 1 or 2 which includes the additional step of isolating 20-dihydro-20-deoxy-23-demycinosyltylosin.

4. The method of claim 1 or 2 which includes the additional step of isolating 20-dihydro-20-deoxy-5-O-mycaminosyltylonolide.

5. A biologically pure culture of *Streptomyces fradiae* ATCC 31733 or a mutant or recombinant thereof which produces 20-dihydro-20-deoxy-23-demycinosyltylosin or 20-dihydro-20-deoxy-5-O-mycaminosyltylonolide.

6. A biologically pure culture of *Streptomyces fradiae* ATCC 31733 of claim 5.

* * * * *